United States Patent
Ning et al.

(10) Patent No.: US 10,350,248 B2
(45) Date of Patent: Jul. 16, 2019

(54) **USES OF *BACTEROIDES* IN TREATMENT OR PREVENTION OF OBESITY AND OBESITY-RELATED DISEASES**

(71) Applicant: RUIJIN HOSPITAL AFFILIATED TO SHANGHAI JIAO TONG UNIVERSITY SCHOOL OF MEDICINE, Shanghai (CN)

(72) Inventors: Guang Ning, Shanghai (CN); Jie Hong, Shanghai (CN); Weiqing Wang, Shanghai (CN); Ruixin Liu, Shanghai (CN); Jiqiu Wang, Shanghai (CN)

(73) Assignee: RUIJIN HOSPITAL AFFILIATED TO SHANGHAI JIAO TONG UNIVERSITY SCHOOL OF MEDICINE, Shanghai (CN)

( * ) Notice: Subject to any disclaimer, the term of this patent is extended or adjusted under 35 U.S.C. 154(b) by 20 days.

(21) Appl. No.: 15/515,343

(22) PCT Filed: Sep. 30, 2014

(86) PCT No.: PCT/CN2014/087994
§ 371 (c)(1),
(2) Date: Mar. 29, 2017

(87) PCT Pub. No.: WO2016/049883
PCT Pub. Date: Apr. 7, 2016

(65) Prior Publication Data
US 2017/0224744 A1  Aug. 10, 2017

(51) Int. Cl.
| | |
|---|---|
| *A61K 35/74* | (2015.01) |
| *A61K 35/747* | (2015.01) |
| *A23L 33/135* | (2016.01) |
| *C12N 1/20* | (2006.01) |
| *A23K 20/10* | (2016.01) |
| *A61K 9/00* | (2006.01) |
| *A61K 47/26* | (2006.01) |

(52) U.S. Cl.
CPC .............. *A61K 35/74* (2013.01); *A23K 20/10* (2016.05); *A23L 33/135* (2016.08); *A61K 9/0056* (2013.01); *A61K 35/747* (2013.01); *A61K 47/26* (2013.01); *C12N 1/20* (2013.01); *A23V 2002/00* (2013.01)

(58) Field of Classification Search
CPC ...... A61K 35/74; A61K 35/747; A23L 33/135
See application file for complete search history.

(56) References Cited

U.S. PATENT DOCUMENTS

2005/0186189 A1* 8/2005 Hsu ...................... A61K 35/747
424/93.45

FOREIGN PATENT DOCUMENTS

| WO | 2008076696 A2 | 6/2008 | |
|---|---|---|---|
| WO | WO-2010020693 A2 * | 2/2010 | ......... A61K 378/465 |
| WO | 2012142605 A1 | 10/2012 | |
| WO | WO-2012142605 A1 * | 10/2012 | ............. A61K 35/74 |
| WO | 2013175038 A1 | 11/2013 | |
| WO | 2014019271 A1 | 2/2014 | |

OTHER PUBLICATIONS

Hong et al. Two New Xylanases With Different Substrate Specificities From the Human Gut Bacterium Bacteroides Intestinalis DSM 17393; Applied and Environmental Microbiology, vol. 80, No. 7, pp. 2084-2093. (Year: 2014).*
Lazar, M. How Obesity Causes Diabetes: Not a Tall Tale; Science, vol. 307, pp. 373-375. (Year: 2005).*
Wang et al. Bacteroides Intestinalis DSM 17393, A Member of the Human Colonic Microbiome, Upregulates Multiple Endoxylanases During Growth on Xylan; Nature: Scientific Reports, vol. 6, No. 34360, pp. 1-11. (Year: 2016).*
Bakir et al., "*Bacteroides intestinalis* sp. nov., isolated from human faeces," International Journal of Systematic and Evolutionary Microbiology, vol. 56, No. Pt. 1, pp. 151-154, Jan. 1, 2006.
Cano et al., "Bacteroides uniformis CECT 7771 Ameliorates Metabolic and Immunological Dysfunction in Mice with High-Fat-Diet Induced Obesity," PLOS ONE, vol. 7, No. 7 p. e41079, Jul. 26, 2012.
EPO, Office Action for EP Application No. 14903005, dated Apr. 26, 2018.
ISA/CN, International Search Report and Written Opinion for PCT/CN2014/087994, dated Jun. 23, 2015.

* cited by examiner

*Primary Examiner* — Paul C Martin
(74) *Attorney, Agent, or Firm* — Hodgson Russ LLP (57) ABSTRACT

Provided are uses of *Bacteroides* in preparation of a medicament. The medicament is for use in treatment or prevention of obesity and obesity-related diseases. Also provided are a pharmaceutical composition, a medicament, a food product, and an animal feed that comprise *Bacteroides*, uses thereof in treatment or prevention of obesity and obesity-related diseases, and a method for treatment or prevention of obesity and obesity-related diseases.

11 Claims, 3 Drawing Sheets

USES OF *BACTEROIDES* IN TREATMENT OR PREVENTION OF OBESITY AND OBESITY-RELATED DISEASES

CROSS-REFERENCE TO RELATED APPLICATION

This application is the U.S. national phase of PCT Application No. PCT/CN2014/087994 filed on Sep. 30, 2014, the entire content of which is incorporated herein by reference.

FIELD

The present disclosure relates to the field of microbiology, and more particularly to use of *Bacteroides* in manufacture of a medicament, also to a pharmaceutical composition, a medicament and a food including *Bacteroides*, and use thereof in treating or preventing obesity and obesity-related diseases.

BACKGROUND

Obesity, a chronic disease, is caused by many factors, but its origin has not been clear so far. Obesity is also an inducing factor to a series of diseases, such as hypertension, diabetes, coronary heart disease, gallbladder disease, osteoarthritis, sleep apnea, respiratory disorder, hysteroma, prostate cancer, breast cancer and colon cancer. It is reported by NIH that there are about 97 million Americans are overweight or over-fat, in which about 15.1 million people suffer from obesity-related type II diabetes, and about 200,000 people die from obesity-related diseases each year.

Obesity is generally caused by excess body fat due to functional changes in physiology or biochemistry. Fat usually includes neutral lipids, phospholipids and cholesterol. Fat increase is due to more energy intake over energy consumption. In terms of pathogenesis, obesity includes two types: (a) simple obesity and (b) secondary obesity. The simple obesity can be divided into idiopathic obesity and acquired obesity, and the number of patients with the simple obesity can account for more than 95% of the total number of patients with obesity. Idiopathic obesity is caused by tremendous adipocytes, and is common in childhood obesity. Acquired obesity is caused by adipocytes in larger size and is common in adult obesity. Secondary obesity, also known as symptomatic obesity, is usually caused by endocrine or metabolic diseases.

At present, there are five strategies for the treatment of obesity: dieting, exercising, behavioral therapy, medical therapy, and therapeutic operation, which strategy or strategies combination is selected primarily depending on health risk factors and the rate and effect of weight loss of a patient. The rate and effect of weight loss of the patient are affected by many factors, such as age, height, family history and risk factors. Diet-exercise therapy, i.e. diet with food with low calorie and low fat in combination with aerobic exercise, needs to be insisted for a long term, is generally considered unsuccessful to general public, however. Surgery for removal of body fat can achieve immediate results, but with many restrictions, such as operation risk, non-persistent effect and high expensive cost.

Presently, medical therapy is the main clinical method for treating obesity and obesity-related diseases (such as diabetes). Mechanisms of medical therapy include appetite suppression, increasement of energy consumption, stimulation of fat movement, reduction of triglyceride synthesis and inhibition of fat absorption. Currently, drugs mainly include: phenylpropanolamine (PPA), orlistat (Xenical III) and sibutramine (Reductil™). Hyperglycemia in some diabetics still cannot be adequately controlled by the diet and/or exercise therapies or use of the above-described therapeutic compounds. For these patients, exogenous insulin should be used, which is not only very expensive and painful, but also will bring about a variety of complications to patients. For example, error calculation to insulin dose caused by lack of food and abnormal exercise will lead to insulin response (hypoglycemia). In addition, use of drugs may also give rise to local or systemic allergies or immune resistance to drugs.

At present, there is no effective method and medicament for treating or preventing obesity and related diseases thereof with fewer side-effects in the related art. Therefore, it is urgently needed in the art to develop a new medicament for treating or preventing obesity and related diseases thereof without toxic side effect.

SUMMARY

Embodiments of the present disclosure seek to solve at least one of the problems existing in the related art to at least some extent. For this, one purpose of embodiments of the present disclosure is to provide the use of *Bacteroides* in treatment or prevention of obesity and obesity-related diseases.

In embodiments of a first aspect of the present disclosure, use of *Bacteroides* in manufacture of a medicament for treating or preventing obesity and obesity-related diseases is provided. Inventors of the present disclosure have found that, administration of the medicament to animals can reduce the body weight and blood glucose of animals effectively, thereby being capable of treating or preventing the obesity and obesity-related diseases, such as diabetes.

In embodiments of the present disclosure, the *Bacteroides* are *Bacteroides intestinalis*, thereby effectively reducing body weight and blood glucose of animals, and further being capable of effectively treating or preventing obesity and obesity-related diseases.

In embodiments of the present disclosure, the *Bacteroides* are at least one selected from *Bacteroides intestinalis* DSM 17393, *Bacteroides intestinalis* JCM 13266, and *Bacteroides intestinalis* AM-1. Therefore, body weight and blood glucose of animals are reduced with a significant effect.

In embodiments of the present disclosure, the obesity-related disease is obesity or diabetes.

In embodiments of the present disclosure, the medicament is used to reduce body weight or blood glucose of animals.

In embodiments of the present disclosure, the animals are mammals, preferably human, murine or leporid.

In embodiments of a second aspect of the present disclosure, a pharmaceutical composition is provided, which includes: *Bacteroides* and/or a metabolite thereof; and a pharmaceutically acceptable adjuvant. Inventors of the present disclosure have surprisingly found that, administration of the pharmaceutical composition of the present disclosure to animals can reduce the body weight and blood glucose of animals effectively, thereby being capable of treating or preventing the obesity and obesity-related diseases effectively.

In embodiments of the present disclosure, the *Bacteroides* are *Bacteroides intestinalis*, thereby effectively reducing body weight and blood glucose of animals, and further being capable of effectively treating or preventing obesity and obesity-related diseases.

In embodiments of the present disclosure, the *Bacteroides* are at least one selected from *Bacteroides intestinalis* DSM 17393, *Bacteroides intestinalis* JCM 13266, and *Bacteroides intestinalis* AM-1, thereby significantly reducing body weight and blood glucose of animals.

In embodiments of the present disclosure, the pharmaceutical composition is in solid form and includes the *Bacteroides* in $1 \times 10^{-1} \times 10^{20}$ cfu/g and/or the metabolite thereof; alternatively the pharmaceutical composition is in liquid form and includes the *Bacteroides* in $1 \times 10^1 \times 10^{20}$ cfu/mL and/or the metabolite thereof. In such a way, the body weight and blood glucose of animals are reduced with an ideal effect, thereby avoiding an un-ideal effect in reduction of the body weight and blood glucose of animals with insufficient *Bacteroides*, and unobvious improvement in reduction of the body weight and blood glucose of animals with excessive *Bacteroides*, which results in unnecessary waste. It should be noted that, the expression "*Bacteroides* in $1 \times 10^{-1} \times 10^{20}$ cfu/g or $1 \times 10^{-1} \times 10^{20}$ cfu/mL and the metabolite thereof" used herein refers to bacteria in a concentration of $1 \times 10^{-1} \times 10^{20}$ cfu/g or $1 \times 10^{-1} \times 10^{20}$ cfu/mL and/or metabolites resulted by the bacteria in such a concentration.

In embodiments of the present disclosure, the pharmaceutical composition is in solid form and includes the *Bacteroides* not less than $1 \times 10^6$ cfu/g and/or the metabolite thereof, preferably *Bacteroides* in $1 \times 10^{11}$ cfu/g or more and/or the metabolite thereof; alternatively the pharmaceutical composition is in liquid form and includes the *Bacteroides* not less than $1 \times 10^6$ cfu/mL and/or the metabolite thereof, preferably *Bacteroides* in $1 \times 10^{11}$ cfu/mL or more and/or the metabolite thereof. In such a way, the body weight and blood glucose of animals are reduced with a better effect.

In embodiments of the present disclosure, the pharmaceutically acceptable adjuvant is at least one selected from carrier, excipient, diluent, lubricant, wetting agent, emulsifier, suspension stabilizer, preservative, sweetener and spice.

In embodiments of the present disclosure, the pharmaceutically acceptable adjuvant is at least one selected from lactose, glucose, sucrose, sorbitol, mannose, starch, arabic gum, calcium phosphate, alginate, gelatin, calcium silicate, fine crystalline cellulose, polyvinylpyrrolidone, cellulose, water, syrup, methylcellulose, methyl hydroxybenzoate, propyl hydroxybenzoate, talc, magnesium stearate, and mineral oil.

In embodiments of the present disclosure, the pharmaceutical composition further includes: at least one of *Lactobacillus gasseri*, *Lactobacillus rhamnosus* GM-020 and *Lactobacillus rhamnosus* PL60. In such a case, it is beneficial to improve the effect in reduction of the body weight and blood glucose of animals.

In embodiments of a third aspect of the present disclosure, a medicament is provided, which includes the pharmaceutical composition described hereinbefore. The medicament according to the present disclosure is capable of effectively reducing body weight and blood glucose of animals, thereby further being capable of treating or preventing obesity and obesity-related diseases, such as diabetes.

In embodiments of the present disclosure, the medicament is in at least one form selected from granules, capsules, tablets, powders, an oral solution, suspension and emulsion. In such a form, the medicament is easy to be administrated.

In embodiments of a fourth aspect of the present disclosure, a food is provided, which includes: *Bacteroides* and/or a metabolite thereof; and an acceptable adjuvant in bromatology. Inventors of the present disclosure have found that, administration of the food to animals can reduce the body weight and blood glucose of animals effectively, thereby being capable of treating or preventing the obesity and obesity-related diseases.

In embodiments of the present disclosure, the *Bacteroides* are *Bacteroides intestinalis*, thereby effectively reducing body weight and blood glucose of animals, and further being capable of treating or preventing obesity and obesity-related diseases.

In embodiments of the present disclosure, the *Bacteroides* are at least one selected from *Bacteroides intestinalis* DSM 17393, *Bacteroides intestinalis* JCM 13266, and *Bacteroides intestinalis* AM-1. Therefore, body weight and blood glucose of animals are reduced with a significant effect.

In embodiments of the present disclosure, the food is in solid form and includes the *Bacteroides* in $1 \times 10^{-1} \times 10^{20}$ cfu/g and/or the metabolite thereof; alternatively the food is in liquid form and includes the *Bacteroides* in $1 \times 10^{-1} \times 10^{20}$ cfu/mL and/or the metabolite thereof. In such a way, the body weight and blood glucose of animals are reduced with an ideal effect, thereby avoiding an un-ideal effect in reduction of the body weight and blood glucose of animals with insufficient *Bacteroides*, and unobvious improvement in reduction of the body weight and blood glucose of animals with excessive *Bacteroides*, which results in unnecessary waste.

In embodiments of the present disclosure, the food is in solid form and includes the *Bacteroides* not less than $1 \times 10^6$ cfu/g and/or the metabolite thereof, preferably *Bacteroides* in $1 \times 10^{11}$ cfu/g or more and/or the metabolite thereof; alternatively the food is in liquid form and includes the *Bacteroides* not less than $1 \times 10^6$ cfu/mL and/or the metabolite thereof, preferably *Bacteroides* in $1 \times 10^{11}$ cfu/mL or more and/or the metabolite thereof. In such a way, the body weight and blood glucose of animals are reduced with a better effect.

In embodiments of the present disclosure, the acceptable adjuvant in bromatology is at least one selected from carrier, excipient, diluent, lubricant, wetting agent, emulsifier, suspension stabilizer, preservative, sweetener and spice.

In embodiments of the present disclosure, the acceptable adjuvant in bromatology is at least one selected from lactose, glucose, sucrose, sorbitol, mannose, starch, arabic gum, calcium phosphate, alginate, gelatin, calcium silicate, fine crystalline cellulose, polyvinylpyrrolidone, cellulose, water, syrup, methylcellulose, methyl hydroxybenzoate, propyl hydroxybenzoate, talc, magnesium stearate, and mineral oil.

In embodiments of the present disclosure, the food further includes: at least one of *Lactobacillus gasseri*, *Lactobacillus rhamnosus* GM-020 and *Lactobacillus rhamnosus* PL60. In such a case, it is beneficial to improve the effect in reduction of the body weight and blood glucose of animals.

In embodiments of the present disclosure, the food is in at least one form selected from solid, dairy, solution, powder and suspension formulations. In such a form, the food is easy to be taken.

In embodiments of a fifth aspect of the present disclosure, a fodder is provided, which includes: *Bacteroides* and a metabolite thereof. The body weight and blood glucose of animals can be effectively reduced through providing animals with the fodder of the present disclosure.

In embodiments of the present disclosure, the *Bacteroides* are *Bacteroides intestinalis*, thereby effectively reducing body weight and blood glucose of animals, and further being capable of treating or preventing obesity and obesity-related diseases.

In embodiments of the present disclosure, the *Bacteroides* are at least one selected from *Bacteroides intestinalis* DSM 17393, *Bacteroides intestinalis* JCM 13266, and *Bacteroides intestinalis* AM-1. Therefore, body weight and blood glucose of animals are reduced with a significant effect.

In embodiments of the present disclosure, the fodder is in solid form and includes the *Bacteroides* in $1\times10^{-1}\times10^{20}$ cfu/g and/or the metabolite thereof; alternatively the fodder is in liquid form and includes the *Bacteroides* in $1\times10^{-1}\times10^{20}$ cfu/mL and/or the metabolite thereof. In such a way, the body weight and blood glucose of animals are reduced with an ideal effect, thereby avoiding an un-ideal effect in reduction of the body weight and blood glucose of animals with insufficient *Bacteroides*, and unobvious improvement in reduction of the body weight and blood glucose of animals with excessive *Bacteroides*, which results in unnecessary waste.

In embodiments of the present disclosure, the fodder is in solid form and includes the *Bacteroides* not less than $1\times10^6$ cfu/g and/or the metabolite thereof, preferably *Bacteroides* in $1\times10^{11}$ cfu/g or more and/or the metabolite thereof; alternatively the fodder is in liquid form and includes the *Bacteroides* not less than $1\times10^6$ cfu/mL and/or the metabolite thereof, preferably *Bacteroides* in $1\times10^{11}$ cfu/mL or more and/or the metabolite thereof. In such a way, the body weight and blood glucose of animals are reduced with a better effect.

In embodiments of a sixth aspect of the present disclosure, use of the pharmaceutical composition, the medicament, or the food described hereinbefore in treating or preventing obesity and obesity-related diseases is provided. Inventors of the present disclosure have found that, administration of the pharmaceutical composition, the medicament or the food described hereinbefore to animals can reduce the body weight and blood glucose of animals effectively, thereby being capable of treating or preventing the obesity and obesity-related diseases.

In embodiments of the present disclosure, the obesity-related disease is obesity or diabetes.

In embodiments of a seventh aspect of the present disclosure, a method for treating or preventing obesity and obesity-related diseases is provided, which includes administering to an animal the pharmaceutical composition, the medicament, or the food described hereinbefore. Administration of the pharmaceutical composition, the medicament or the food described hereinbefore to animals can reduce the body weight and blood glucose of animals effectively, thereby being capable of treating or preventing the obesity and obesity-related diseases.

It should be appreciated that, within the scope of the present disclosure, technical features described hereinbefore and specifically described hereinafter (e.g., in examples) may be combined with each other to form a new or preferred technical solution, which will not be elaborated herein.

DETAILED DESCRIPTION

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al., *Molecular Cloning: A Laboratory Manual* (New York: Cold Spring Harbor Laboratory Press, 1989)) or *Microbiology: A Laboratory Manual* (edited by James Cappuccino and Natalie Sherman, Pearson Education Press)); or in accordance with the product instructions.

*Bacteroides* have the following physiological characteristics: in rod-like, with a size of about 0.8 μm×1~5.0 μm, without spores, unmovable, and presented in scattered state. *Bacteroides* can ferment several kinds of carbohydrates (including glucose, lactose, sucrose, maltose, xylose, Arabia sugar, cellobiose, mannose, raffinose and rhamnose) to produce acid. *Bacteroides* are cultured under an anaerobic condition in a modified PYG medium (DSMZ Medium 104) for 1 to 2 days at 37° C. Inventors of the present disclosure have unexpectedly found through extensive and in-depth study and experiment that, *Bacteroides* have functions in treatment or prevention of obesity and obesity-related diseases, and the active composition containing *Bacteroides*, after fed to experimental subjects, can suppress weight gain and lower blood glucose of the experimental subjects, and effectively alleviate symptoms, such as diabetes and obesity.

Therefore, in embodiments of the first aspect of the present disclosure, use of *Bacteroides* in manufacture of a medicament for treating or preventing obesity and obesity-related diseases is provided. Inventors of the present disclosure have found that, administration of the medicament to animals can reduce the body weight and blood glucose of animals effectively, thereby being capable of treating or preventing the obesity and obesity-related diseases, such as diabetes.

In embodiments of the present disclosure, the *Bacteroides* are *Bacteroides intestinalis*, thereby effectively reducing body weight and blood glucose of animals, and further being capable of effectively treating or preventing obesity and obesity-related diseases.

In embodiments of the present disclosure, the *Bacteroides* are at least one selected from *Bacteroides intestinalis* DSM 17393 (DSM 17393), *Bacteroides intestinalis* JCM 13266 (JCM 13266) and *Bacteroides intestinalis* AM-1 (AM-1). Therefore, body weight and blood glucose of animals are reduced with a significant effect.

In embodiments of the present disclosure, the obesity-related disease is obesity or diabetes.

In embodiments of the present disclosure, the *Bacteroides* are used to reduce body weight or blood glucose of animals.

In embodiments of the present disclosure, the animals are mammals, preferably human, murine or leporid.

According to embodiments of the present disclosure, Bacterial strains DSM 17393, JCM 13266 and AM-1 all have the ability to suppress weight gain of subjects who intake high-fat foods. According to embodiments of the present invention, as compared with untreated control groups, CF57BL/6J mice, fed with high fat foods that can cause obesity, can maintain their weight without significant weight gain after treated with strains DSM 17393, JCM 13266 and AM-1, respectively, which also contribute to lower blood glucose. Thus, it is demonstrated that those strains can be used in treatment or prevention of obesity and obesity-related diseases, such as diabetes.

In embodiments of a second aspect of the present disclosure, a pharmaceutical composition is provided, which includes: *Bacteroides* and/or a metabolite thereof and a pharmaceutically acceptable adjuvant. Inventors of the present disclosure have surprisingly found that, administration of the pharmaceutical composition of the present disclosure to animals can reduce the body weight and blood glucose of animals effectively, thereby being capable of treating or preventing the obesity and obesity-related diseases effectively.

In embodiments of the present disclosure, the *Bacteroides* are *Bacteroides intestinalis*, thereby effectively reducing body weight and blood glucose of animals, and further being capable of effectively treating or preventing obesity and obesity-related diseases.

In embodiments of the present disclosure, the *Bacteroides* are at least one selected from *Bacteroides intestinalis* DSM 17393, *Bacteroides intestinalis* JCM 13266, and *Bacteroides intestinalis* AM-1, thereby significantly reducing body weight and blood glucose of animals.

In embodiments of the present disclosure, the pharmaceutical composition is in solid form and includes the *Bacteroides* in $1\times10^{-1}\times10^{20}$ cfu/g and/or the metabolite thereof; alternatively the pharmaceutical composition is in liquid form and includes the *Bacteroides* in $1\times10^{-1}\times10^{20}$ cfu/mL and/or the metabolite thereof. In such a way, the body weight and blood glucose of animals are reduced with an ideal effect, thereby avoiding an un-ideal effect in reduction of the body weight and blood glucose of animals with insufficient *Bacteroides*, and unobvious improvement in reduction of the body weight and blood glucose of animals with excessive *Bacteroides*, which results in unnecessary waste.

In embodiments of the present disclosure, the pharmaceutical composition is in solid form and includes the *Bacteroides* not less than $1\times10^6$ cfu/g and/or the metabolite thereof, preferably *Bacteroides* in $1\times10^{11}$ cfu/g or more and/or the metabolite thereof alternatively the pharmaceutical composition is in liquid form and includes the *Bacteroides* not less than $1\times10^6$ cfu/mL and/or the metabolite thereof, preferably *Bacteroides* in $1\times10^{11}$ cfu/mL or more and/or the metabolite thereof. In such a way, the body weight and blood glucose of animals are reduced with a better effect.

In embodiments of the present disclosure, the pharmaceutically acceptable adjuvant is at least one selected from carrier, excipient, diluent, lubricant, wetting agent, emulsifier, suspension stabilizer, preservative, sweetener and spice.

In embodiments of the present disclosure, the pharmaceutically acceptable adjuvant is at least one selected from lactose, glucose, sucrose, sorbitol, mannose, starch, arabic gum, calcium phosphate, alginate, gelatin, calcium silicate, fine crystalline cellulose, polyvinylpyrrolidone, cellulose, water, syrup, methylcellulose, methyl hydroxybenzoate, propyl hydroxybenzoate, talc, magnesium stearate, and mineral oil.

In embodiments of the present disclosure, the pharmaceutical composition further includes: at least one of *Lactobacillus gasseri*, *Lactobacillus rhamnosus* GM-020 and *Lactobacillus rhamnosus* PL60. In such a case, it is beneficial to improve the effect in reduction of the body weight and blood glucose of animals.

In embodiments of a third aspect of the present disclosure, a medicament is provided, which includes the pharmaceutical composition described hereinbefore. The medicament according to the present disclosure is capable of effectively reducing body weight and blood glucose of animals, thereby further being capable of treating or preventing obesity and obesity-related diseases, such as diabetes.

In embodiments of the present disclosure, the medicament is in at least one form selected from granules, capsules, tablets, powders, an oral solution, suspension and emulsion. In such a form, the medicament is easy to be administrated.

In embodiments of the present disclosure, the medicament may also be administrated in any form selected from tablets, injections and capsules, and may include excipients, medicament allowable media and carriers. Those substances may be selected depending on administration routes.

In some embodiments of the present disclosure, the medicament can be produced as enteric-coating formulations by a variety of well-known methods, such that active ingredients of the medicament, i.e. microorganisms (*Bacteroides*), can successfully pass through the stomach without destroyed by gastric acid.

In further embodiments, the microorganisms of the present disclosure may be used in the form of capsules prepared by conventional methods. For example, the standard excipients and the cold-dry microorganisms of the present disclosure are mixed to be made into pellets, which are then filled into gelatin capsules. In addition, the microorganisms of the present disclosure may be mixed with pharmaceutically allowable excipients, such as liquid glues, cellulose, silicates or mineral oils, to be made into suspensions or dispersions, which may be further filled into soft gelatin capsules.

In further embodiments, the medicament of the present disclosure may be formulated into enteric-coating tablets for oral use. Term "enteric-coating" used herein includes all coatings allowable to be used in conventional medicaments. These coatings cannot be degraded by gastric acid but fully degraded in small intestine and rapidly release the microorganisms of the present disclosure. The enteric-coating of the present disclosure may be maintained in a synthetic stomach acid (such as HCl solution with pH=1) for 2 hours or more at 36-38° C. and preferably degraded in a synthetic intestinal solution (such as buffer solution with pH=7.0) within 1.0 hour.

Each tablet is coated with an enteric-coating material in about 16-30 mg per tablet, preferably about 16-25 mg per tablet, more preferably about 16-20 mg. In the present disclosure, the enteric-coating is of a thickness of 5 to 100 μm, and ideally 20 to 80 μm. The enteric-coating material is selected from conventionally known polymers. Preferred enteric-coating of the present disclosure is made from cellulose acetate phthalate polymer or cellulose acetate trimellitate polymer as well as methacrylic acid copolymer (for example, methacrylic acid copolymer containing 40% or more of methacrylic acid and containing methylcellulose hydroxypropyl phthalate or ester derivatives thereof).

The cellulose acetate phthalate used in the enteric-coating of the present disclosure is of a viscosity of about 45 to 90 cp, an acetyl content of 17 to 26%, and a content of phthalic acid of 30 to 40%. The cellulose acetate trimellitate used in the enteric-coating is of a viscosity of about 5 to 21 cs and an acetyl content of 17-26%. The cellulose acetate trimellitate produced by Eastman Kodak may be used as the enteric-coating material of the present disclosure.

The hydroxypropyl methylcellulose phthalate used in the enteric-coating of the present disclosure is of a molecular weight of typically from 20,000 to 130,000 daltons, and ideally from 80,000 to 100,000 daltons, a hydroxypropyl content of 5 to 10%, a methoxyl content of 18 to 24%, a phthalyl content of 21 to 35%.

The hydroxypropyl methylcellulose phthalate used for the enteric-coating of the present disclosure is HP50 produced by Shin-Etsu Chemidnl Co. Ltd. HP50 contains a hydroxypropyl content of 6 to 10%, a methoxyl content of 20 to 24% and a propyl content of 21 to 27%, and is of a molecular weight of 84,000 daltons. Another enteric-coating material used in the present disclosure is HP55, which contains a content of hydroxypropyl methylcellulose phthalate of 5 to 9%, a methoxyl content of 18 to 22%, a content of phthalic acid of 27 to 35%, and is of a molecular weight of 78,000 daltons.

The enteric-coating of the present disclosure may be prepared by spraying an enteric-coating solution onto a core through conventional methods. Solvents used in this process are alcohols (e.g., ethanol), ketones (e.g., acetone), halogenated hydrocarbon compounds (such as dichloromethane) or combinations thereof. A softener, such as dibutyl phthalate and glyceryl triacetate, are added into the enteric-coating solution in a ratio of about 0.5 part or about 0.3 part softener to 1 part enteric-coating substance. The spraying process is preferably carried out continuously and the amount of sprayed materials can be controlled according to the coating conditions. Spraying pressure may be optionally adjusted, and a desired result generally may be obtained under an average pressure of 1 to 1.5 bars.

It should be noted that, the expression "pharmaceutically effective amount" used herein refers to such an amount that may be functional or active to humans and/or animals and acceptable to humans and/or animals. For example, in the present disclosure, it is possible to prepare a medicament formulation containing *Bacteroides* in $1\times10^{-1}\times10^{20}$ cfu/ml or $1\times10^{-1}\times10^{20}$ cfu/g particular, $1\times10^{4}\text{-}1\times10^{15}$ cfu/mL or $1\times10^{4}\text{-}1\times10^{15}$ cfu/g, and more specifically, $1\times10^{6}\text{-}1\times10^{11}$ cfu/ml or $1\times10^{6}\text{-}1\times10^{11}$ cfu/g) and/or metabolites thereof.

When used for preparing the medicament, the effective dose of *Bacteroides* or metabolites thereof used may vary depending on the administration mode and the severity degree of the disease to be treated. Dosage suitable for oral administration includes *Bacteroides* in about $1\times10^{-1}\times10^{20}$ cfu/g or about $1\times10^{-1}\times10^{20}$ cfu/ml (in particular, about $1\times10^{4}\text{-}1\times10^{15}$ cfu/g or about $1\times10^{4}\text{-}1\times10^{15}$ cfu/mL, and more specifically, about $1\times10^{6}\text{-}1\times10^{11}$ cfu/g or about $1\times10^{6}\text{-}1\times10^{11}$ cfu/ml) and/or active ingredients produced by fermentation which are intimately mixed with a pharmaceutically acceptable carrier in solid or liquid state. Such dosage regimen may be adjusted to provide the best therapeutic response, as required. For example, several separate doses may be administrated daily or doses may be administrated in a reduced proportion, according to the urgent requirement of the treatment condition.

*Bacteroides* or metabolites thereof described in the present disclosure may be administrated by oral. Solid carriers include: starch, lactose, dicalcium phosphate, microcrystalline cellulose, sucrose and porcellanite, and liquid carriers include: medium, polyethylene glycol, nonionic surfactants and edible oils (such as, corn oil, peanut oil and sesame oil), as long as they are suitable for characteristics of *Bacteroides* or metabolites thereof and the specific administration ways required. Adjuvants commonly used in the preparation of medicaments may also be advantageously included, such as, flavoring agents, pigments, preservatives and antioxidants, e.g., vitamin E, vitamin C, BHT and BHA.

Viewing from ease preparation and administration, the medicament is preferably in solid form, in particular tablets and capsules filled with solid or liquid. Oral administration is the preferred administration way.

The medicament of the present disclosure may be administrated to the subject by once or more times a day. Dosage unit presents such a dosage that is formally distinguishable and suitable for use in humans or all other mammalian individuals. Each unit contains a pharmaceutically acceptable carrier and an effective therapeutic amount of the microorganism of the present disclosure. Administration dosage varies depending on the body weight and the severity degree of obesity of the patient, supplemental active ingredients contained therein and the microorganisms used. In addition, administration may be performed separately if possible, and continuously if desired. Therefore, the administration dosage used herein will not limit the present disclosure.

In embodiments of a fourth aspect of the present disclosure, a food is provided, which includes: *Bacteroides* and/or a metabolite thereof; and an acceptable adjuvant in bromatology.

In embodiments of the present disclosure, the *Bacteroides* are *Bacteroides intestinalis*, thereby effectively reducing body weight and blood glucose of animals, and further being capable of treating or preventing obesity and obesity-related diseases.

In embodiments of the present disclosure, the *Bacteroides* are at least one selected from *Bacteroides intestinalis* DSM 17393, *Bacteroides intestinalis* JCM 13266, and *Bacteroides intestinalis* AM-1. Therefore, body weight and blood glucose of animals are reduced with a significant effect.

In embodiments of the present disclosure, the food is in solid form and includes the *Bacteroides* in $1\times10^{-1}\times10^{20}$ cfu/g and/or the metabolite thereof; alternatively the food is in liquid form and includes the *Bacteroides* in $1\times10^{-1}\times10^{20}$ cfu/mL and/or the metabolite thereof. In such a way, the body weight and blood glucose of animals are reduced with an ideal effect, thereby avoiding an un-ideal effect in reduction of the body weight and blood glucose of animals with insufficient *Bacteroides*, and unobvious improvement in reduction of the body weight and blood glucose of animals with excessive *Bacteroides*, which results in unnecessary waste.

In embodiments of the present disclosure, the food is in solid form and includes the *Bacteroides* not less than $1\times10^{6}$ cfu/g and/or the metabolite thereof, preferably *Bacteroides* in $1\times10^{11}$ cfu/g or more and/or the metabolite thereof; alternatively the food is in liquid form and includes the *Bacteroides* not less than $1\times10^{6}$ cfu/mL and/or the metabolite thereof, preferably *Bacteroides* in $1\times10^{11}$ cfu/mL or more and/or the metabolite thereof. In such a way, the body weight and blood glucose of animals are reduced with a better effect.

In embodiments of the present disclosure, the acceptable adjuvant in bromatology is at least one selected from carrier, excipient, diluent, lubricant, wetting agent, emulsifier, suspension stabilizer, preservative, sweetener and spice.

In embodiments of the present disclosure, the acceptable adjuvant in bromatology is at least one selected from lactose, glucose, sucrose, sorbitol, mannose, starch, arabic gum, calcium phosphate, alginate, gelatin, calcium silicate, fine crystalline cellulose, polyvinylpyrrolidone, cellulose, water, syrup, methylcellulose, methyl hydroxybenzoate, propyl hydroxybenzoate, talc, magnesium stearate, and mineral oil.

In embodiments of the present disclosure, the food further includes: at least one of *Lactobacillus gasseri, Lactobacillus rhamnosus* GM-020 and *Lactobacillus rhamnosus* PL60. In such a case, it is beneficial to improve the effect in reduction of the body weight and blood glucose of animals.

In embodiments of the present disclosure, the food is in at least one form selected from solid, dairy, solution, powder and suspension formulations. In such a form, the food is easy to be taken.

In embodiments of a fifth aspect of the present disclosure, a fodder is provided, which includes: *Bacteroides* and a metabolite thereof. The body weight and blood glucose of animals can be effectively reduced through providing animals with the fodder of the present disclosure.

In embodiments of the present disclosure, the *Bacteroides* are *Bacteroides intestinalis*, thereby effectively reducing body weight and blood glucose of animals, and further being capable of treating or preventing obesity and obesity-related diseases.

In embodiments of the present disclosure, the *Bacteroides* are at least one selected from *Bacteroides intestinalis* DSM 17393, *Bacteroides intestinalis* JCM 13266, and *Bacteroides intestinalis* AM-1. Therefore, body weight and blood glucose of animals are reduced with a significant effect.

In embodiments of the present disclosure, the fodder is in solid form and includes the *Bacteroides* in $1 \times 10^{-1} \times 10^{20}$ cfu/g and the metabolite thereof; alternatively the fodder is in liquid form and includes the *Bacteroides* in $1 \times 10^{-1} \times 10^{20}$ cfu/mL and/or the metabolite thereof. In such a way, the body weight and blood glucose of animals are reduced with an ideal effect, thereby avoiding an un-ideal effect in reduction of the body weight and blood glucose of animals with insufficient *Bacteroides*, and unobvious improvement in reduction of the body weight and blood glucose of animals with excessive *Bacteroides*, which results in unnecessary waste.

In embodiments of the present disclosure, the fodder is in solid form and includes the *Bacteroides* not less than $1 \times 10^6$ cfu/g and/or the metabolite thereof, preferably *Bacteroides* in $1 \times 10^{11}$ cfu/g or more and/or the metabolite thereof; alternatively the fodder is in liquid form and includes the *Bacteroides* not less than $1 \times 10^6$ cfu/mL and/or the metabolite thereof, preferably *Bacteroides* in $1 \times 10^{11}$ cfu/mL or more and/or the metabolite thereof. In such a way, the body weight and blood glucose of animals are reduced with a better effect.

In embodiments of a sixth aspect of the present disclosure, use of the pharmaceutical composition, the medicament, or the food described hereinbefore in treating or preventing obesity and obesity-related diseases is provided. Inventors of the present disclosure have found that, administration of the pharmaceutical composition, the medicament or the food described hereinbefore to animals can reduce the body weight and blood glucose of animals effectively, thereby being capable of treating or preventing the obesity and obesity-related diseases.

In embodiments of the present disclosure, the obesity-related disease is obesity or diabetes.

In embodiments of a seventh aspect of the present disclosure, a method for treating or preventing obesity and obesity-related diseases is provided, which includes administering to an animal the pharmaceutical composition, the medicament, or the food described hereinbefore. Administration of the pharmaceutical composition, the medicament or the food described hereinbefore to animals can reduce the body weight and blood glucose of animals effectively, thereby being capable of treating or preventing the obesity and obesity-related diseases.

Embodiment 1

1. Experimental Materials

Mice: a total of 25 C57BL/6J Mice (purchased from Experimental Animal Center of Southern Medical University), 6 weeks old, were normally fed with the same food and raised in the same environment.

Bacterial strains: *Bacteroides intestinalis* DSM 17393, purchased from DSMZ (Deutsche Sammlung von Mikroorganismen and Zellkulturen GmbH); *Bacteroides intestinalis* JCM 13266, purchased from JCM (Japan Collection of Microorganisms); *Bacteroides intestinalis* AM-1, from Laboratory of Microbial Physiology, Research Faculty of Agriculture, Hokkaido University.

High fat foods (HF): containing 58% lard, 25.6% carbohydrate, 16.4% protein, purchased from Beijing HFK Bioscience Co. Ltd.

Conventional mice food: purchased from Experimental Animal Center of Southern Medical University.

2. Mice Grouping and Induction Treatment

In this embodiment, the mice were randomly divided into 5 groups with 5 mice for each group.

Figure 1:
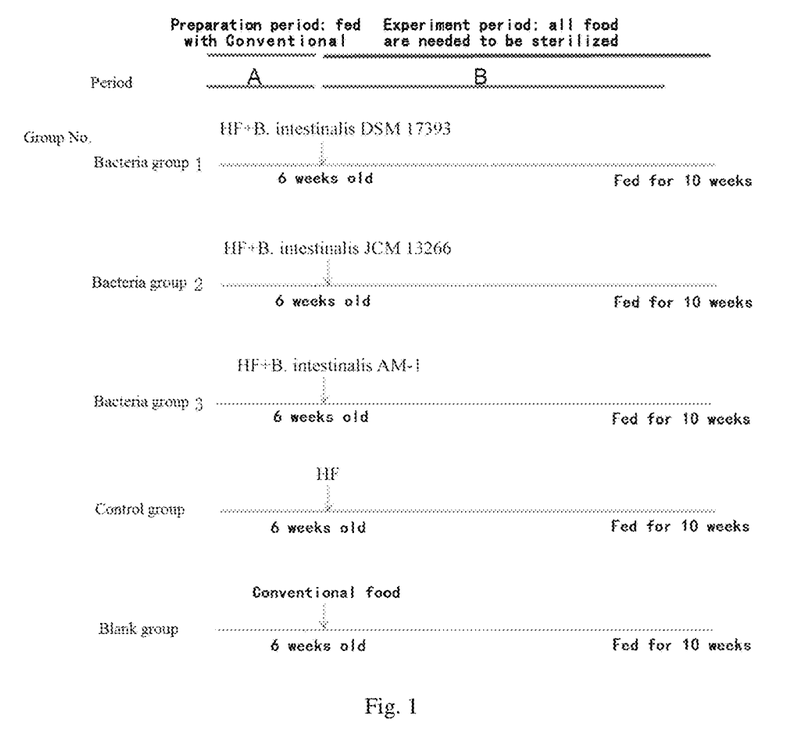
FIG. 1 shows a protocol of grouping and treatment of experimental mice according to an embodiment of the present disclosure.

C57BL/6J Mice, 6 weeks old, normally fed (without sterility), were selected for the experiment. *Bacteroides* DSM 17393, JCM 13266 and AM-1 to be tested were introduced into the intestinal tract of mice by feeding method, respectively. Insulin tolerances of mice were identified by oral glucose tolerance test (OGTT). Specific experimental grouping information and processing steps are shown in FIG. 1. The experimental steps were as follows.

25 mice were normally fed to 6 weeks old under the same environment (food without sterility), feeding amounts were recorded. Weight changes and physical conditions of the mice were regularly monitored.

25 mice were averagely divided into 5 experimental groups (5 mice for each experimental group), each of which was placed in a clean bench, and true experimental period thus began. A first feeding change was performed according to the experimental design.

The mice must live in the corresponding incubator and cannot exchange during the experiment. The incubator was kept to be clean. Feeding was performed timely and quantitatively via gavage and with a uniform standard for all mice.

Bacteria was fed via gavage once every two days in accordance with 0.15 mL bacteria/10 g of body weight, where the bacteria is of a concentration of $1 \times 10^7$ cfu/mL and a concentrated concentration of $1 \times 10^8$ cfu/mL. Bacteria solution was cultured in advance, and activated weekly to keep fresh and measured to determine its concentration.

During the experiment, data (such as the body weights, body lengths and food intakes of the mice) were recorded and blood glucose levels of the mice were measured by glucometer every week. Symptoms and time points at which diabetes appeared were recorded for each group. Determination method of the blood glucose tolerance: fasting blood glucoses were firstly determined after the mice were starved for 10 hours, then postprandial blood glucoses were determined after 60 min and 120 min since the mice were fed with the glucose solution, respectively.

3. Experimental Results (1) Results of weight gain of individual group of the mice after fed for 10 weeks are shown in Table 1 and FIG. 2.

TABLE 1

| Groups | Time (weeks) | | | | | | | | | | |
|---|---|---|---|---|---|---|---|---|---|---|---|
| | 0 | 1 | 2 | 3 | 4 | 5 | 6 | 7 | 8 | 9 | 10 |
| HF + *B. intestinalis* DSM 17393 | 0.00 | 0.90 | 1.55 | 2.10 | 2.48 | 3.04 | 4.13 | 4.82 | 5.40 | 5.96 | 6.12 |
| HF + *B. intestinalis* JCM 13266 | 0.00 | 1.18 | 2.31 | 3.04 | 3.62 | 4.26 | 5.37 | 5.97 | 6.49 | 7.72 | 8.44 |
| HF + *B. intestinalis* AM-1 | 0.00 | 0.96 | 1.66 | 2.25 | 3.05 | 3.63 | 4.76 | 5.36 | 6.37 | 6.75 | 7.62 |
| Control group (HF) | 0.00 | 1.50 | 2.60 | 3.54 | 4.70 | 5.36 | 6.04 | 7.04 | 9.28 | 10.33 | 11.35 |
| Blank group (Conventional food) | 0.00 | 0.55 | 1.08 | 1.47 | 1.76 | 2.21 | 2.91 | 3.50 | 3.49 | 4.37 | 4.66 |

Figure 3:
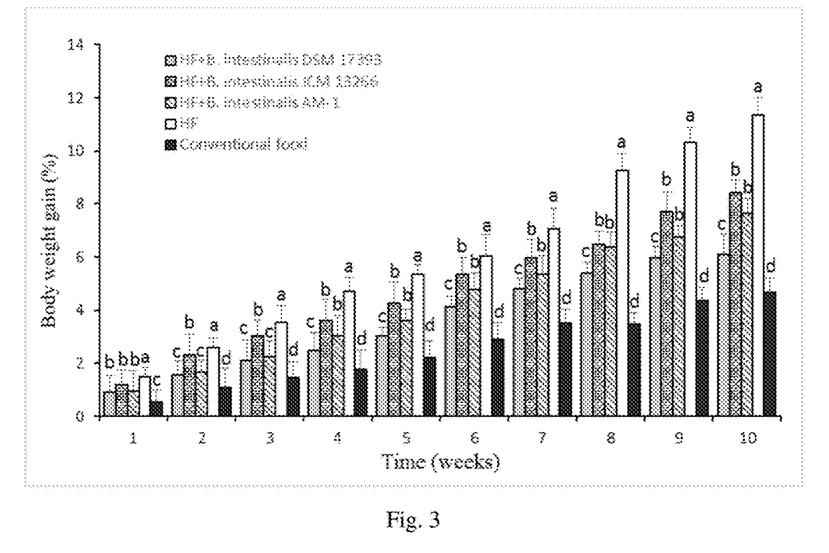
FIG. 3 shows comparison results of P values for indicating differences in weight gain among mice in the three groups within 10 weeks according to an embodiment of the present disclosure.

(2) Analysis results indicating significant differences in weight gain among individual group of the mice after fed for 10 weeks are shown in FIG. 3.

Figure 2:
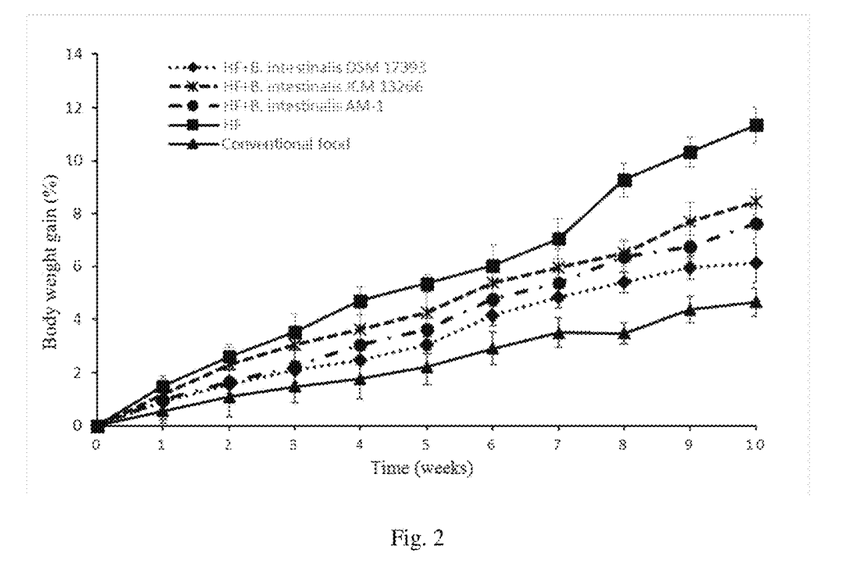
FIG. 2 shows weight gain increasing trends among mice in three groups within 10 weeks according to an embodiment of the present disclosure.

It can be seen from the results shown in Table 1, FIG. 2 and FIG. 3 that, body weights of obese mice can be significantly reduced by feeding the mice with the bacteria to be tested for 10 weeks.

Figure 4:
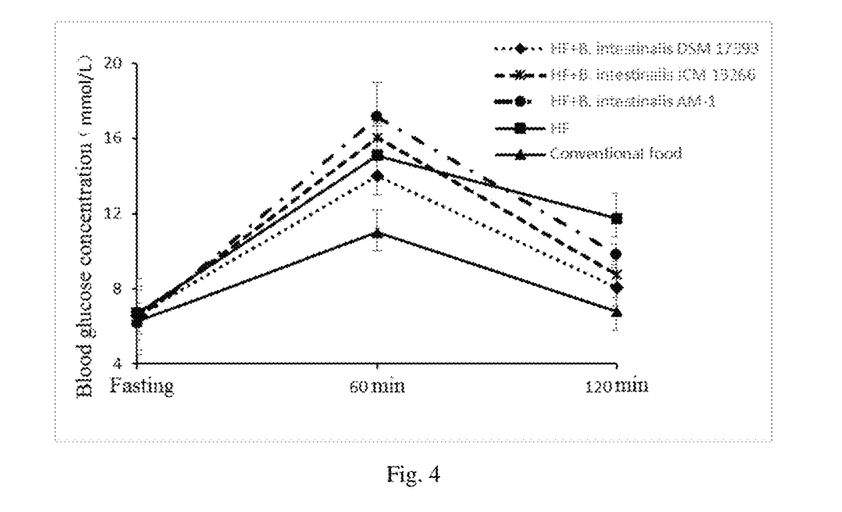
FIG. 4 is a curve showing changes in blood glucose of mice at week 10 according to an embodiment of the present disclosure.
Figure 5:
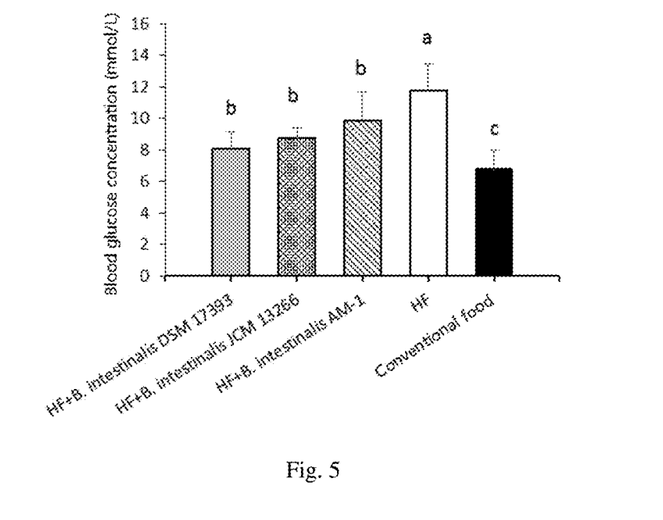
FIG. 5 shows glucose tolerance of mice (comparison of blood glucose values of mice after 120 min fed with glucose solution) at week 10 according to an embodiment of the present disclosure.

(3) Determination results of blood glucose contents of individual group of the mice fed at 10 weeks are shown in Table 2, FIG. 4 and FIG. 5.

TABLE 2

| Groups | Blood glucose concentration (mmol/L) | | |
|---|---|---|---|
| | Fasting | 60 min | 120 min |
| HF + *B. intestinalis* DSM 17393 | 6.59 ± 1.97 | 13.99 ± 1.07 | 8.08 ± 1.05 |
| HF + *B. intestinalis* JCM 13266 | 6.43 ± 1.72 | 16.02 ± 0.62 | 8.77 ± 0.68 |
| HF + *B. intestinalis* AM-1 | 6.21 ± 1.72 | 17.15 ± 1.83 | 9.83 ± 0.54 |
| Control group (HF) | 6.72 ± 1.39 | 15.07 ± 1.72 | 11.74 ± 1.36 |
| Blank group (Conventional food) | 6.25 ± 0.99 | 11.00 ± 1.20 | 6.78 ± 0.75 |

It can be seen from the results shown in Table 2 and FIG. 4 that, blood glucoses of obese mice can be significantly reduced by feeding the mice with the bacteria to be tested. It can be seen from the results shown in FIG. 5 that, the blood glucose tolerances of obese mice can be significantly improved by feeding the mice with the bacteria to be tested. Therefore, it is demonstrated that *Bacteroides* can be effectively used to reduce the body weight and blood glucose.

Embodiment 2: Formulation of the Food

In this embodiment, food containing *Bacteroides intestinalis* DSM 17393, *Bacteroides intestinalis* JCM 13266 and *Bacteroides intestinalis* AM-1 were formulated, respectively. Details were shown as follows:

1. Materials and proportions thereof used to formulating the food are shown in Table 3.

TABLE 3

| Materials | Mass percentage (%) |
|---|---|
| *Bacteroides intestinalis* DSM 17393 or *Bacteroides intestinalis* JCM 13266 or *Bacteroides intestinalis* AM-1 | 0.5 |
| Milk | 90.0 |
| White sugar | 9.5 |

Milk and white sugar were mixed in accordance with the formula and proportions shown in Table 3, then stirred until completely mixed, homogenized at a pressure of 20 MPa subsequent to preheated, then sterilized for 5 to 10 min at about 90° C., followed by cooled to 40 to 43° C. to obtain a mixture, per gram of which was then inoculated with *Bacteroides intestinalis* DSM 17393, *Bacteroides intestinalis* JCM 13266 or *Bacteroides intestinalis* AM-1 in 1-100× $10^6$ cfu to obtain the food.

Embodiment 3: Formulation of the Pharmaceutical Composition

In this embodiment, pharmaceutical compositions containing *Bacteroides intestinalis* DSM 17393, *Bacteroides intestinalis* JCM 13266 and *Bacteroides intestinalis* AM-1 were formulated, respectively. Details were shown as follows.

Materials and proportions thereof used to formulating the pharmaceutical composition are shown in Table 4

| Materials | Mass percentage (%) |
|---|---|
| *Bacteroides intestinalis* DSM 17393 or *Bacteroides intestinalis* JCM 13266 or *Bacteroides intestinalis* AM-1 | 1.0 |
| Lactose | 2.0 |
| Yeast powder | 2.0 |
| Peptone | 1.0 |
| Pure water | 94.0 |

Lactose, yeast powder, peptone and pure water were mixed in accordance with the proportions shown in Table 4 to be uniform, then preheated to 60 to 65° C., followed by homogenized at a pressure of 20 MPa, then sterilized for 20 to 30 min at about 90° C., followed by cooled to 36 to 38° C., then inoculated with *Bacteroides intestinalis* DSM 17393, *Bacteroides intestinalis* JCM 13266 or *Bacteroides intestinalis* AM-1 in an inoculum concentration of 1-50×$10^6$ cfu/mL, followed by fermented at 36 to 38° C. to make the pH reach 6.0, and then centrifuged, following freeze-dried to obtain a freeze-dried product containing *Bacteroides intestinalis* DSM 17393 or *Bacteroides intestinalis* JCM 13266 or *Bacteroides intestinalis* AM-1 and with a moisture content less than 3%. 0.5 g freeze-dried product was mixed with same amount maltodextrin, and the obtained mixture was filled into capsules so as to obtain capsules containing *Bacteroides intestinalis* DSM 17393 or *Bacteroides intestinalis* JCM 13266 or *Bacteroides intestinalis* AM-1.

Embodiment 4: Formulation of the Fodder

Devices:
1. Seeding tank (GYS-500C);
2. Fermentation tank (GYS-1500C);
3. Fermentation incubator (SPX-1500);
4. Pulverizer (SWFL82D);
5. Horizontal pressure steam sterilizer (ZY.01.001);

6. High-speed centrifuging and spraying drier (LPG1000);
7. Heat shrink packaging machine (SM-4525L);
8. Quantitative powder filling machine (DXDCF2000A);
9. Pelletizer First, dry power formulations containing *Bacteroides intestinalis* DSM 17393, *Bacteroides intestinalis* JCM 13266 or *Bacteroides intestinalis* AM-1 were formulated in accordance with solid fermentation method, respectively. The specific steps were as follows.

1. Preparation of Bacteria
(1) Activation of Bacteria

A tube containing bacteria frozen in glycerinum was placed at room temperature until the liquid contained therein was completely melted, then opened near a flame. The liquid was homogenized by blowing up and down the liquid with a 200 μl pipettor. Then, 200 μl liquid, taken from the frozen tube with the pipettor, was inoculated into 50 ml fresh modified PYG liquid medium and cultured on a shaker for 24 h under 160 r/min at 37° C. to obtain activated bacteria.

(2) Amplified Culture

The above-mentioned activated bacteria was inoculated into the fresh modified PYG medium at a proportion of 3% and cultured on the shaker for 24 h under 160 r/min at 37° C. to obtain amplified bacteria.

2. Solid Fermentation
(1) Formulation and Sub-Distribution of Solid Fermentation Medium Suitable amount of wheat bran was weighed and mixed with water at a mass ratio of 1:1-2 to be uniform. The obtained mixture was sterilized for 15 to 20 min at a high temperature of 115° C. to obtain the solid fermentation medium. Then, on an operating table, the solid fermentation medium with a temperature not lower than 70° C. was sub-distributed into sterilized clean fermentation dishes and the wheat bran agglomerated in the solid fermentation medium was pinched to be scattered.

(2) Inoculation

The amplified bacteria mentioned above were inoculated into the solid fermentation medium at an inoculation amount of 1 to 5%. The obtained mixture was poured into individual fermentation dish after stirred to be uniform, and then fermented for 48 h at 37° C. to obtain the fermented wheat bran.

3. Fermentation of Fermented Wheat Bran

The fermented wheat bran obtained above was dried in a drying oven for 12 to 16 h at a constant temperature of 60° C. Then, the dried and fermented wheat bran was pulverized with a sieve in 100 meshes to obtain a viable dry powder formulation, which was bagged for preservation. Some samples were left for viable counting. The viable dry powder formulation containing 100 million to 200 million bacteria per gram was selected to use.

Thus, the viable dry powder formulations containing *Bacteroides intestinalis* DSM 17393, *Bacteroides intestinalis* JCM 13266 or *Bacteroides intestinalis* AM-1 was respectively formulated to obtain fodder additives. Finally, the obtained fodder additives was added into the feedstuff of an animal fodder in an addition amount of 0.1%, then extruding granulated by a granulator to obtain the fodders containing *Bacteroides intestinalis* DSM 17393, *Bacteroides intestinalis* JCM 13266 or *Bacteroides intestinalis* AM-1 as fodder additive, respectively.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, it will be appreciated to those skilled in the art that different embodiments or examples as well as features in different embodiments or examples described in this specification may be combined without contradictory circumstances.

Although explanatory embodiments have been shown and described, it would be appreciated by those skilled in the art that the above embodiments are explanatory and cannot be construed to limit the present disclosure, and changes, alternatives, and modifications can be made in the embodiments without departing from spirit, principles and scope of the present disclosure.

What is claimed is:

1. A method for treating or preventing obesity and treating diabetes, comprising administering to an animal a pharmaceutical composition containing *Bacteroides intestinalis* DSM 17393, wherein the pharmaceutical composition is capable of reducing body weight or blood glucose of the animal.

2. The method according to claim 1, wherein the animal is a mammal.

3. The method according to claim 1, wherein the animal is human, murine or leporid.

4. The method according to claim 1, wherein the pharmaceutical composition further comprises a pharmaceutically acceptable adjuvant selected from at least one of carrier, excipient, diluent, lubricant, wetting agent, emulsifier, suspension stabilizer, preservative, sweetener and spice.

5. The method according to claim 4, wherein the pharmaceutically acceptable adjuvant is at least one selected from lactose, glucose, sucrose, sorbitol, mannose, starch, arabic gum, calcium phosphate, alginate, gelatin, calcium silicate, fine crystalline cellulose, polyvinylpyrrolidone, cellulose, water, syrup, methylcellulose, methyl hydroxybenzoate, propyl hydroxybenzoate, talc, magnesium stearate, and mineral oil.

6. The method according to claim 1, wherein the pharmaceutical composition further comprises at least one of *Lactobacillus gasseri*, *Lactobacillus rhamnosus* GM-020 and *Lactobacillus rhamnosus* PL60.

7. The method according to claim 1, wherein the pharmaceutical composition is formulated into a medicament in at least one form selected from granules, capsules, tablets, powders, an oral solution, suspension and emulsion.

8. The method according to claim 1, wherein the pharmaceutical composition is formulated into a food or fodder in at least one form selected from solid, dairy, solution, powder and suspension formulations.

9. The method according to claim 1, wherein
the pharmaceutical composition is in solid form and comprises the *Bacteroides intestinalis* DSM 17393 in concentration of $1 \times 10 - 1 \times 10^{20}$ cfu/g, or
the pharmaceutical composition is in liquid form and comprises the *Bacteroides intestinalis* DSM 17393 in concentration of $1 \times 10 - 1 \times 10^{20}$ cfu/mL.

10. The method according to claim 1, wherein
the pharmaceutical composition is in solid form and comprises the *Bacteroides intestinalis* DSM 17393 in a concentration of not less than $1\times10^6$ cfu/g, or
the pharmaceutical composition is in liquid form and comprises the *Bacteroides intestinalis* DSM 17393 in a concentration of not less than $1\times10^6$ cfu/mL.

11. The method according to claim 1, wherein
the pharmaceutical composition is in solid form and comprises the *Bacteroides intestinalis* DSM 17393 in a concentration of $1\times10^{11}$ cfu/g or more, or
the pharmaceutical composition is in liquid form and comprises the *Bacteroides intestinalis* DSM 17393 in a concentration of $1\times10^{11}$ cfu/mL.

* * * * *